United States Patent
Markovitz et al.

(10) Patent No.: US 11,344,236 B2
(45) Date of Patent: May 31, 2022

(54) SYSTEM AND METHOD FOR GENERATING ELECTROPHYSIOLOGY MAPS

(71) Applicant: St. Jude Medical, Cardiology Division, Inc., St. Paul, MN (US)

(72) Inventors: Craig Markovitz, Mahtomedi, MN (US); Louis-Philippe Richer, Montreal (CA); Chunlan Jiang, Northridge, CA (US); Cyrille Casset, Saint Selve (FR)

(73) Assignee: ST JUDE MEDICAL CARDIOLOGY DIVISION, INC., St Paul, MN (US)

( * ) Notice: Subject to any disclaimer, the term of this patent is extended or adjusted under 35 U.S.C. 154(b) by 236 days.

(21) Appl. No.: 16/461,236

(22) PCT Filed: Nov. 16, 2017

(86) PCT No.: PCT/US2017/062037
§ 371 (c)(1),
(2) Date: May 15, 2019

(87) PCT Pub. No.: WO2018/094063
PCT Pub. Date: May 24, 2018

(65) Prior Publication Data
US 2019/0307344 A1    Oct. 10, 2019

Related U.S. Application Data

(60) Provisional application No. 62/424,779, filed on Nov. 21, 2016.

(51) Int. Cl.
*A61B 5/02*    (2006.01)
*A61B 5/25*    (2021.01)
(Continued)

(52) U.S. Cl.
CPC ............... *A61B 5/25* (2021.01); *A61B 5/339* (2021.01); *A61B 5/7225* (2013.01); *A61B 5/742* (2013.01); *G16H 50/20* (2018.01); *G16H 50/50* (2018.01)

(58) Field of Classification Search
CPC .................. A61B 18/1492; A61B 2018/00839
See application file for complete search history.

(56) References Cited

U.S. PATENT DOCUMENTS 5,697,377 A   12/1997   Wittkampf
5,983,126 A   11/1999   Wittkampf
(Continued)

FOREIGN PATENT DOCUMENTS

WO    2012/092016    7/2012

OTHER PUBLICATIONS

Written Opinion and International Search Report for PCT/US2017/062037, dated Mar. 2, 2018.

*Primary Examiner* — Michael J D'Abreu
(74) *Attorney, Agent, or Firm* — Wiley Rein LLP

(57) ABSTRACT

A method of generating an electrophysiology map of a portion of a patient's anatomy using an electroanatomical mapping system, includes defining a plurality of inclusion criteria, collecting a plurality of electrophysiology data points, each being associated with inclusion data, and identifying those electrophysiology data points that have inclusion data satisfying the inclusion criteria. The inclusion criteria can then be automatically adjusted to drive the number of electrophysiology data points having inclusion data satisfying the inclusion criteria towards a target number. A graphical representation of the electrophysiology map can be rendered using the final set of electrophysiology data points.

16 Claims, 7 Drawing Sheets

(51) Int. Cl.
  *A61B 5/00* (2006.01)
  *G16H 50/20* (2018.01)
  *G16H 50/50* (2018.01)
  *A61B 5/339* (2021.01)

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2011/0054559 A1* | 3/2011 | Rosenberg ............ A61N 1/3684 607/28 |
| 2013/0274562 A1* | 10/2013 | Ghaffari ............. A61B 5/02055 600/301 |
| 2015/0057507 A1 | 2/2015 | Koyrakh et al. |
| 2016/0324485 A1 | 11/2016 | Erdemir et al. |

\* cited by examiner

SYSTEM AND METHOD FOR GENERATING ELECTROPHYSIOLOGY MAPS

CROSS-REFERENCE TO RELATED APPLICATIONS

This application claims the benefit of U.S. provisional application No. 62/424,779, filed 21 Nov. 2016, which is hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for generating an electrophysiology map from data collected by a roving electrophysiology probe.

Electrophysiological mapping, and more particularly electrocardiographic mapping, is a part of numerous cardiac diagnostic and therapeutic procedures. As the complexity of such procedures increases, however, the electrophysiology maps utilized must increase in quality, in density, and in the rapidity and ease with which they can be generated.

BRIEF SUMMARY

Disclosed herein is a method of generating an electrophysiology map of a portion of a patient's anatomy using an electroanatomical mapping system, including: defining a plurality of inclusion criteria; collecting a plurality of electrophysiology data points, each electrophysiology data point being associated with inclusion data; the electroanatomical mapping system determining a subset of the plurality of electrophysiology data points having associated inclusion data that satisfies the plurality of inclusion criteria and that includes a number of electrophysiology data points; setting a target number of electrophysiology data points from the plurality of electrophysiology data points for inclusion in the electrophysiology map of the portion of the patient's anatomy, the target number being different from the number of electrophysiology data points in the subset; the electroanatomical mapping system automatically modifying the plurality of inclusion criteria; and the electroanatomical mapping system determining a subset of the plurality of electrophysiology data points having associated inclusion data that satisfies the modified plurality of inclusion criteria and that includes a number of electrophysiology data points. The method can also include generating a graphical representation of the electrophysiology map using the subset of the plurality of electrophysiology data points having associated inclusion data that satisfies the modified plurality of inclusion criteria.

In aspects of the disclosure, the step of the electroanatomical mapping system automatically modifying the plurality of inclusion criteria includes the electroanatomical mapping system automatically adding an additional inclusion criterion to the plurality of inclusion criteria. Alternatively or additionally, the step of the electroanatomical mapping system automatically modifying the plurality of inclusion criteria can include the electroanatomical mapping system automatically adjusting at least one inclusion criterion of the plurality of inclusion criteria, and optionally adjusting all inclusion criteria of the plurality of inclusion criteria.

According to embodiments disclosed herein, the step of the electroanatomical mapping system automatically adjusting at least one inclusion criterion of the plurality of inclusion criteria includes: identifying a distribution of the inclusion data for the subset of the plurality of electrophysiology data points having associated inclusion data that satisfies the plurality of inclusion criteria; and determining, using the distribution of the inclusion data, which inclusion criteria of the plurality of inclusion criteria would need to be adjusted a least amount when automatically adjusting the at least one inclusion criteria in order for the subset of the plurality of electrophysiology data points having associated inclusion data that satisfies the modified plurality of inclusion criteria to include the target number of electrophysiology data points.

According to additional embodiments disclosed herein, the step of the electroanatomical mapping system automatically modifying the plurality of inclusion criteria comprises: the electroanatomical mapping system automatically modifying the plurality of inclusion criteria to be more inclusive if the target number is greater than the number of electrophysiology data points in the subset of the plurality of electrophysiology data points having associated inclusion data that satisfies the plurality of inclusion criteria; and the electroanatomical mapping system automatically modifying the plurality of inclusion criteria to be less inclusive if the target number is less than the number of electrophysiology data points in the subset of the plurality of electrophysiology data points having associated inclusion data that satisfies the plurality of inclusion criteria.

It is contemplated that the step of setting a target number of electrophysiology data points from the plurality of electrophysiology data points for inclusion in the electrophysiology map of the portion of the patient's anatomy includes: displaying a graphical inclusion criterion sensitivity control at a neutral sensitivity; accepting user input to adjust the graphical inclusion criterion sensitivity from the neutral sensitivity to an adjusted sensitivity; and the electroanatomical mapping system automatically computing the target number of electrophysiology data points using the adjusted sensitivity and the number of electrophysiology data points in the subset of the plurality of electrophysiology data points having associated inclusion data that satisfies the plurality of inclusion criteria. The electroanatomical mapping system can use a number of electrophysiology data points in the plurality of data points in computing the target number of electrophysiology data points.

In aspects of the disclosure, the method also includes: iteratively repeating the steps: the electroanatomical mapping system automatically modifying the plurality of inclusion criteria; and the electroanatomical mapping system determining a subset of the plurality of electrophysiology data points having associated inclusion data that satisfies the modified plurality of inclusion criteria and that includes a number of electrophysiology data points, until the number of electrophysiology data points in the subset of the plurality of electrophysiology data points having associated inclusion data that satisfies the modified plurality of inclusion criteria reaches the target number of data points for inclusion in the electrophysiology map. A graphical representation of the electrophysiology map can be generated using the subset of the plurality of electrophysiology data points having associated inclusion data that satisfies the modified plurality of inclusion criteria.

In additional aspects of the disclosure, the method also includes: iteratively repeating the steps: the electroanatomical mapping system automatically modifying the plurality of inclusion criteria; and the electroanatomical mapping system determining a subset of the plurality of electrophysiology data points having associated inclusion data that satisfies the modified plurality of inclusion criteria and that includes a number of electrophysiology data points, until a first event to occur of: the number of electrophysiology data points in the subset of the plurality of electrophysiology data points having associated inclusion data that satisfies the modified plurality of inclusion criteria reaches the target number of data points for inclusion in the electrophysiology map, and the electroanatomical mapping system has automatically modified the plurality of inclusion criteria by a preset threshold amount relative to a state of the plurality of inclusion criteria prior to any modification by the electroanatomical mapping system. If the first event to occur is the electroanatomical mapping system has automatically modified the plurality of inclusion criteria by a preset threshold amount relative to a state of the plurality of inclusion criteria prior to any modification by the electroanatomical mapping system, then: the electroanatomical mapping system can automatically reset the plurality of inclusion criteria to the state of the plurality of inclusion criteria prior to any modification by the electroanatomical mapping system; and the electroanatomical mapping system can automatically add one or more additional inclusion criteria to the plurality of inclusion criteria.

After the one or more additional inclusion criteria are added to the plurality of inclusion criteria, the method can also include: iteratively repeating the steps: the electroanatomical mapping system automatically modifying the plurality of inclusion criteria; and the electroanatomical mapping system determining a subset of the plurality of electrophysiology data points having associated inclusion data that satisfies the modified plurality of inclusion criteria and that includes a number of electrophysiology data points, until a first event to occur of: the number of electrophysiology data points in the subset of the plurality of electrophysiology data points having associated inclusion data that satisfies the modified plurality of inclusion criteria reaches the target number of data points for inclusion in the electrophysiology map, and the electroanatomical mapping system has automatically modified the plurality of inclusion criteria by a preset threshold amount relative to a state of the plurality of inclusion criteria prior to any modification by the electroanatomical mapping system. An error can be output if the first event to occur is the electroanatomical mapping system has automatically modified the plurality of inclusion criteria by a preset threshold amount relative to a state of the plurality of inclusion criteria prior to any modification by the electroanatomical mapping system.

Also disclosed herein is a method of generating an electrophysiology map of a portion of a patient's anatomy using an electroanatomical mapping system, including the steps of: receiving a plurality of electrophysiology data points in the electroanatomical mapping system, each electrophysiology data point having associated inclusion data; and the electroanatomical mapping system automatically adjusting one or more inclusion criteria such that a number of electrophysiology data points in a subset of the plurality of electrophysiology data points having associated inclusion data that satisfy the one or more inclusion criteria equals a target number.

The step of the electroanatomical mapping system automatically adjusting one or more inclusion criteria such that a number of electrophysiology data points in a subset of the plurality of electrophysiology data points having associated inclusion data that satisfy the one or more inclusion criteria equals a target number can include the electroanatomical mapping system iteratively automatically adjusting the one or more inclusion criteria until the number of electrophysiology data points in a subset of the plurality of electrophysiology data points having associated inclusion data that satisfy the one or more inclusion criteria equals a target number.

In additional embodiments, the step of the electroanatomical mapping system automatically adjusting one or more inclusion criteria such that a number of electrophysiology data points in a subset of the plurality of electrophysiology data points having associated inclusion data that satisfy the one or more inclusion criteria equals a target number can include the electroanatomical mapping system: identifying a distribution of the inclusion data for the subset of the plurality of electrophysiology data points having associated inclusion data that satisfy the one or more inclusion criteria; and determining, using the distribution of the inclusion data, which inclusion criteria of the one or more inclusion criteria would need to be adjusted a least amount when automatically adjusting the one or more inclusion criteria in order for the subset of the plurality of electrophysiology data points having associated inclusion data that satisfies the one or more inclusion criteria to include the target number of electrophysiology data points.

The instant disclosure also provides a system for generating an electrophysiology map of a portion of a patient's anatomy, including: an inclusion processor configured to: receive as input a plurality of electrophysiology data points, each electrophysiology data point being associated with inclusion data; receive as input a plurality of inclusion criteria; receive as input a target number of electrophysiology data points for inclusion in an electrophysiology map; determine a subset of the plurality of electrophysiology data points having associated inclusion data that satisfy the plurality of inclusion criteria; automatically modify the plurality of inclusion criteria; and determine a subset of the plurality of electrophysiology data points having associated inclusion data that satisfy the modified plurality of inclusion criteria. The system can also include a mapping processor configured to generate a graphical representation of the electrophysiology map from the subset of the plurality of electrophysiology data points having associated inclusion data that satisfy the modified plurality of inclusion criteria.

The inclusion processor can be configured to automatically modify the plurality of inclusion criteria by: automatically modifying the plurality of inclusion criteria to be more inclusive if the target number is greater than a number of electrophysiology data points in the subset of the plurality of electrophysiology data points having associated inclusion data that satisfy the plurality of inclusion criteria; and automatically modifying the plurality of inclusion criteria to be less inclusive if the target number is less than the number of electrophysiology data points in the subset of the plurality of electrophysiology data points having associated inclusion data that satisfy the plurality of inclusion criteria.

The inclusion processor can be configured to iteratively automatically modify the plurality of inclusion criteria until a number of electrophysiology data points in the subset of the plurality of electrophysiology data points having associated inclusion data that satisfy the modified plurality of inclusion criteria equals the target number.

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses and systems for the creation of electrophysiology maps (e.g., electrocardiographic maps). For purposes of illustration, several exemplary embodiments will be described in detail herein in the context of a cardiac electrophysiology procedure. It is contemplated, however, that the methods, apparatuses, and systems described herein can be utilized in other contexts.

Figure 1:
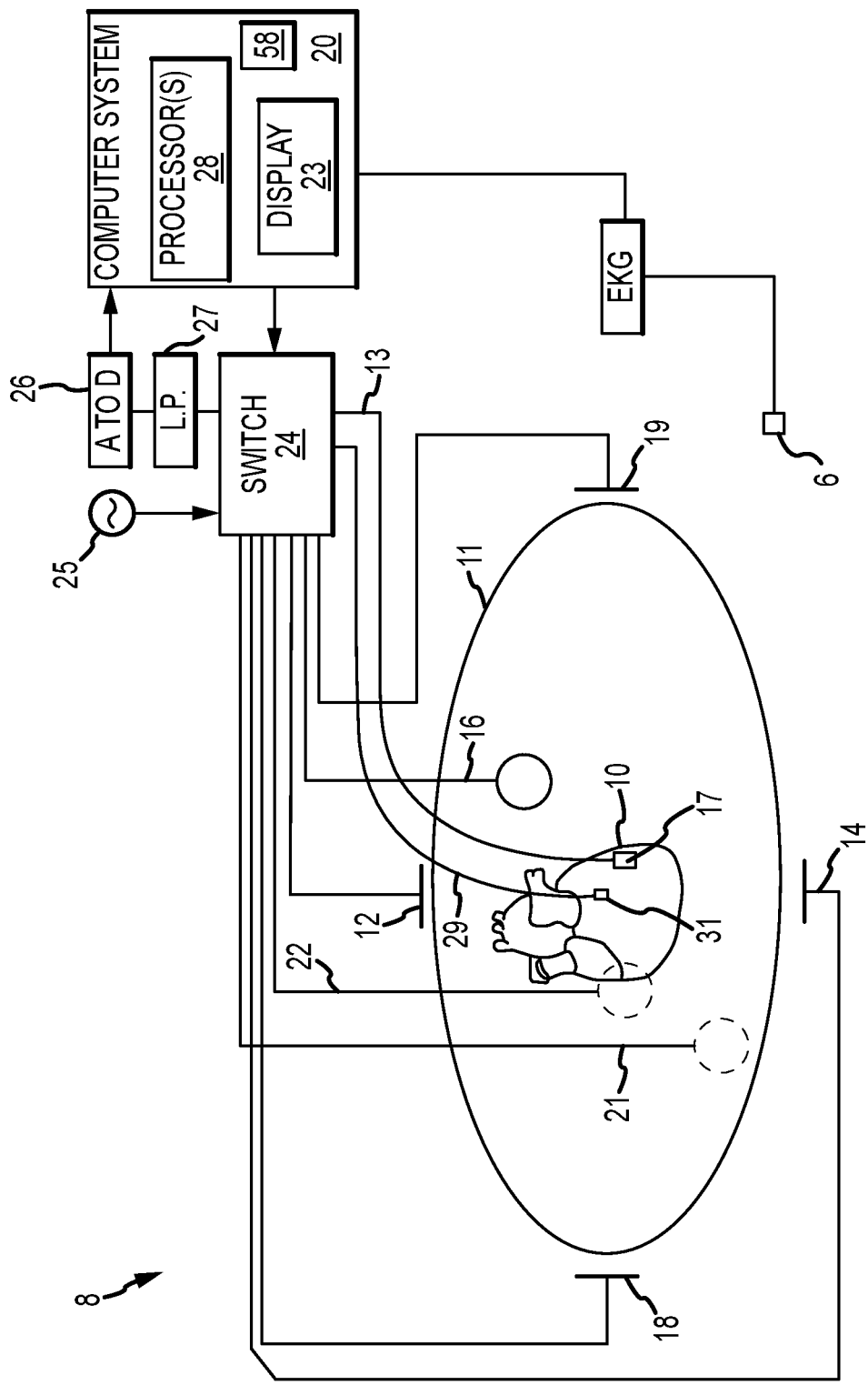
FIG. 1 is a schematic diagram of an electroanatomical mapping system, such as may be used in an electrophysiology study.

FIG. 1 shows a schematic diagram of an exemplary system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, the leads and their connections to computer system 20 are not illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, system 8 may comprise sixty-four electrodes on twelve catheters disposed within the heart and/or vasculature of the patient. Of course, this embodiment is merely exemplary, and any number of electrodes and catheters may be used.

Figure 2:
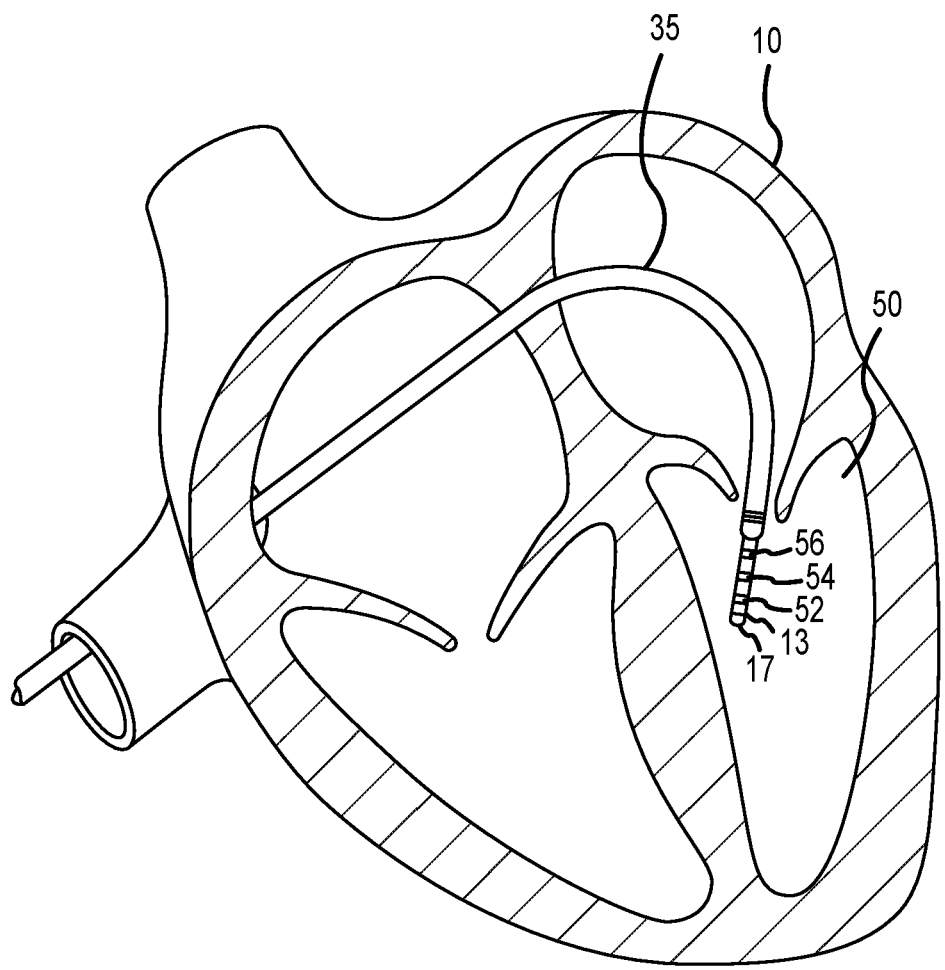
FIG. 2 depicts an exemplary catheter used in an electrophysiology study.

Likewise, it should be understood that catheter 13 (or multiple such catheters) are typically introduced into the heart and/or vasculature of the patient via one or more introducers (not shown in FIG. 1, but readily understood by the ordinarily skilled artisan). For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in, for example, U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another localization system that relies upon electrical fields. Other localization systems, however, may be used in connection with the present teachings, including for example, systems that utilize magnetic fields instead of or in addition to electrical fields for localization. Examples of such systems include, without limitation, the CARTO navigation and location system of Biosense Webster, Inc., the AURORA® system of Northern Digital Inc., Sterotaxis' NIOBE® Magnetic Navigation System, as well as MediGuide™ Technology and the EnSite™ Precision™ system, both from St. Jude Medical, Inc.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

System 8 further includes an inclusion criteria adjustment module 58 operable to automatically adjust inclusion criteria such that more or fewer electrophysiology data points are included in an electrophysiology map according to the teachings herein.

Figure 3:
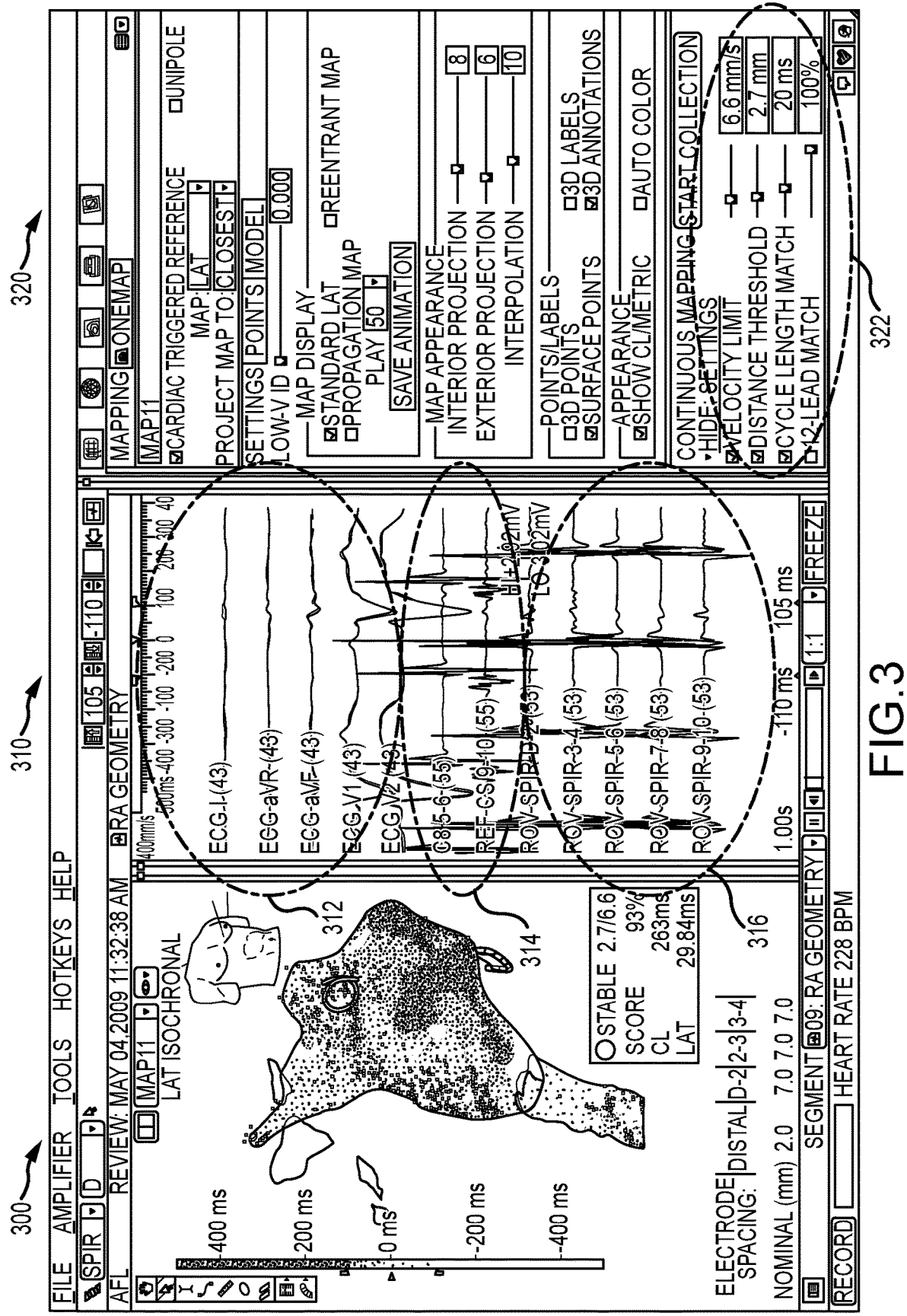
FIGS. 3 and 4 depict exemplary electrophysiology maps.
Figure 4:
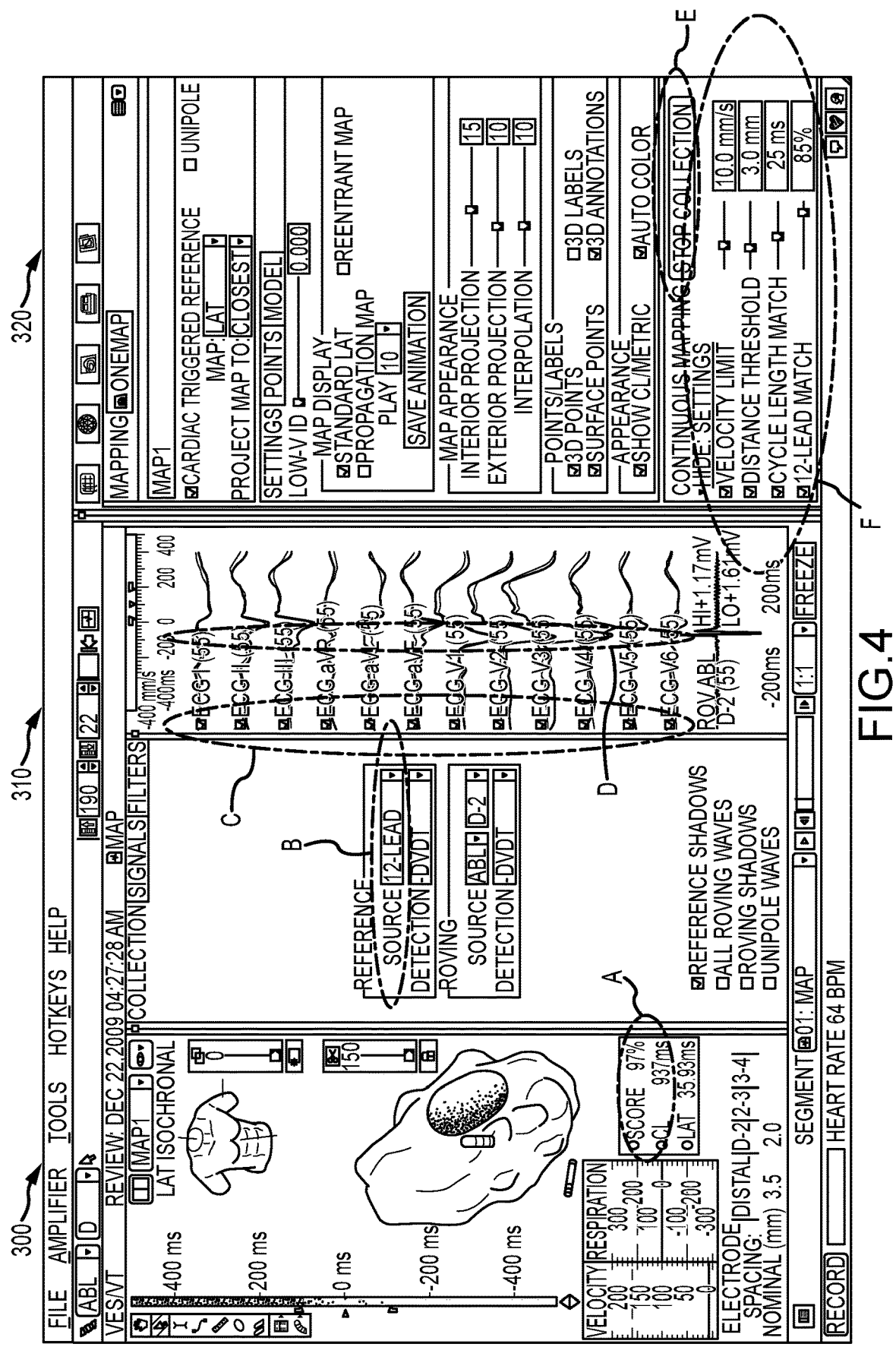

FIGS. 3 and 4 depict exemplary electrophysiology maps generated using various aspects disclosed herein and data collected and processed utilizing system 8 (e.g., using computer system 20). In general, those of ordinary skill in the art will be familiar with the content of FIGS. 3 and 4. Thus, the aspects thereof will only be described herein to the extent necessary to understand the instant disclosure.

FIGS. 3 and 4 each depict an exemplary interface, such as may be output on display 23, including, at the lower right hand corner of leftmost panel 300, a "heads up" display (callout "A" in FIG. 4). The "heads up" display provides feedback regarding the current status of certain inclusion criteria. More particularly, the "heads up" display provides information and visual cues (e.g., the use of red text to indicate that the current inclusion data does not satisfy the corresponding inclusion criterion) regarding the status of the inclusion criteria that are selected using the inclusion criterion control panel, shown at the bottom of rightmost panel 320 (callout "F" in FIG. 4). The "heads up" display and control panel can appear at other locations on the screen.

FIGS. 3 and 4 depict alternative configurations for center panel 310. In FIG. 3, center panel 310 displays the signals from five EKG leads (e.g., traces 312), from two reference electrodes (e.g., traces 314), and from five roving electrodes (e.g., traces 316). In FIG. 4, center panel 310 displays the signals from twelve EKG leads. It also includes check boxes (callout "C") that can be used to enable or disable the signals from various leads for morphology comparison and/or classification purposes.

Figure 5:
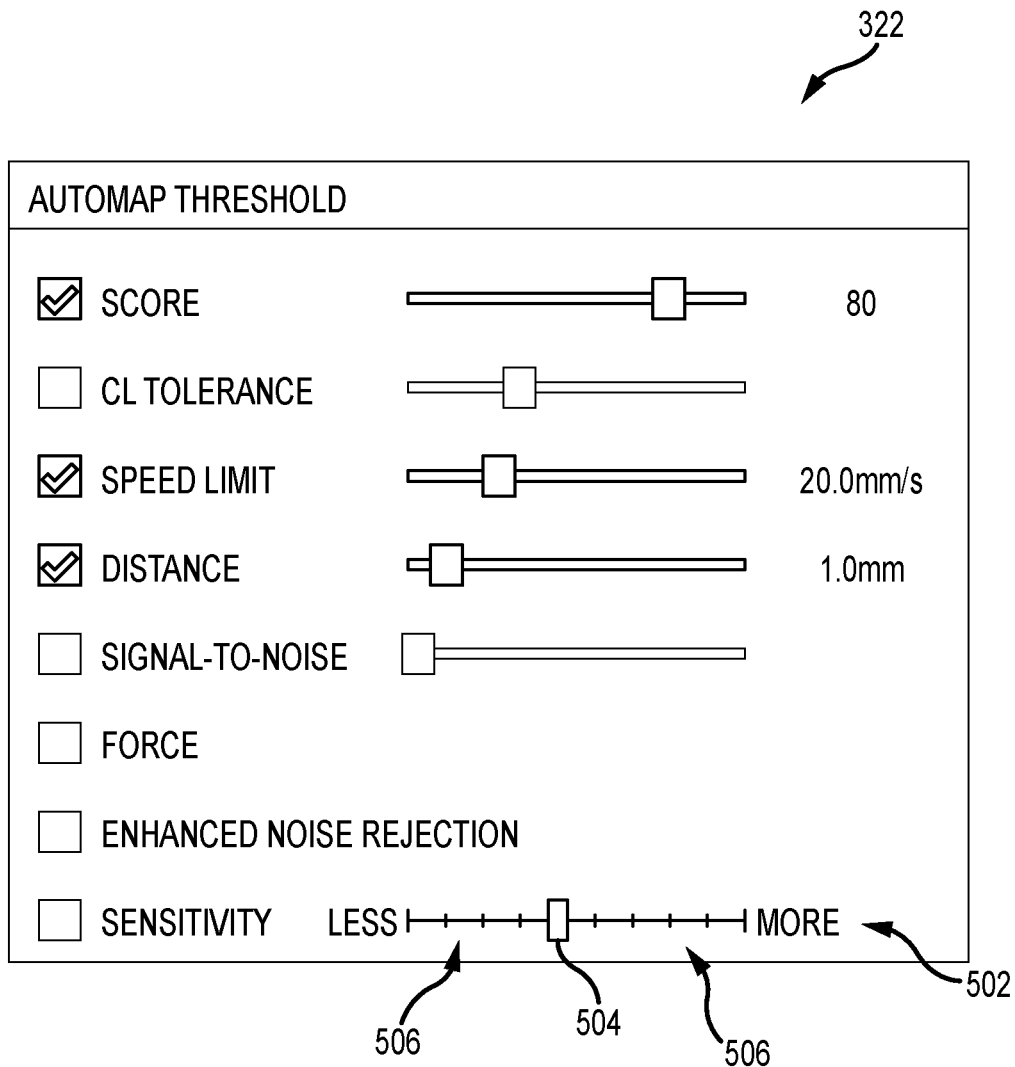
FIG. 5 is an exemplary inclusion criterion control panel/interface.

As shown in FIGS. 3 and 4, the control panel in rightmost panel 320 includes check boxes to determine which inclusion criteria will be applied to collected electrophysiology data points. Likewise, rightmost panel 320 also includes an interface 322 (e.g., sliders) to adjust the inclusion criteria. FIG. 5 is a close-up view of an exemplary inclusion criterion control panel interface 322.

Figure 6A:
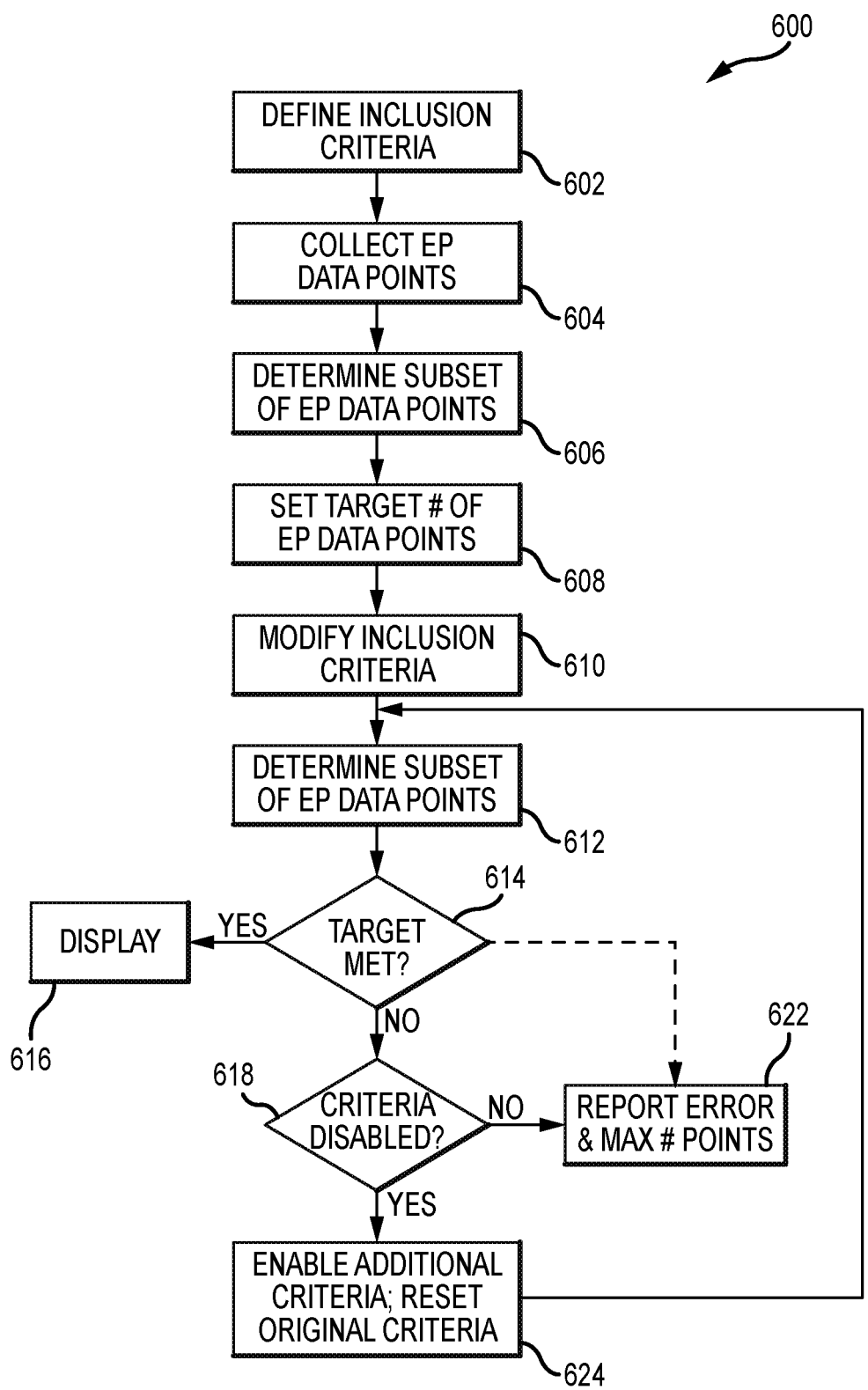
FIG. 6A is a flowchart depicting representative steps that can be followed in a method of generating an electrophysiology map according to aspects of the teachings herein.

One exemplary method of automatically adjusting inclusion criteria will be explained herein with reference to the flowchart 600 of representative steps presented as FIG. 6A. In some embodiments, for example, flowchart 600 may represent several exemplary steps that can be carried out by the computer 20 of FIG. 1 (e.g., by processor 28, including inclusion criteria adjustment module 58). It should be understood that the representative steps described below can be either hardware- or software-implemented. For the sake of explanation, the term "signal processor" is used herein to describe both hardware- and software-based implementations of the teachings herein.

In block 602, a plurality of inclusion criteria are defined. Exemplary inclusion criteria include, but are not limited to, those shown in FIG. 5 (e.g., morphology matching score; cycle length tolerance; catheter speed; catheter distance moved; signal to noise ratio; contact force). The use of inclusion criteria in the creation of electrophysiology maps is described, for example, in U.S. patent application Ser. No. 14/462,128, filed 18 Aug. 2014, which is hereby incorporated by reference as though fully set forth herein.

In block 604, a plurality of electrophysiology data points are collected, for example using one or more electrodes on catheter 13. As the ordinarily skilled artisan will appreciate, each electrophysiology data point includes both electrophysiology data and location data (e.g., information regarding the location of catheter 13 and/or the electrodes 17, 52, 54, 56 thereon, allowing the measured electrophysiology information to be associated with a particular location in space). It also includes (or is associated with) inclusion data that can be used to determine, with reference to one or more inclusion criteria as described below, whether or not the electrophysiology data point should be added to an electrophysiology map. The inclusion data for a particular electrophysiology data point can be displayed in the "heads up" display included in leftmost panel 300 at the time of collection.

In block 606, system 8 determines a subset of the plurality of electrophysiology data points collected in block 604 that are associated with inclusion data that satisfies the inclusion criteria defined in block 602. This subset can be understood as the electrophysiology data points that initially make up the electrophysiology map.

The number of electrophysiology data points that are initially included in the electrophysiology map may not be desirable, however. Thus, in block 608, a target number of electrophysiology data points for inclusion in an electrophysiology map can be set by a user of system 8. The target number will typically be different from the number of electrophysiology data points in the subset determined in block 606. For example, if the user considers the initial subset over-inclusive, the target number can be set lower. On the other hand, if the user considers the initial subset under-inclusive, the target number can be set higher.

According to aspects of the disclosure, the target number of electrophysiology data points can be set and/or adjusted using an inclusion criterion sensitivity control 502, which can be presented as part of interface 322 (FIG. 5). For example, FIG. 5 shows an inclusion criterion sensitivity control 502 including a slider 504 at an initial, neutral setting, which can correspond to the inclusion criteria initially defined in block 602. Rather than adjusting inclusion criteria on an individual basis through interface 322, a user can instead adjust the position of slider 504 from the neutral sensitivity to an adjusted sensitivity (represented, for example, by notches 506 on sensitivity control 502). As slider 504 is so adjusted, system 8 can automatically adjust the inclusion criteria accordingly.

For example, moving slider 504 to the right of neutral can indicate that the user wants more of the collected electrophysiology data points to be included in the electrophysiology map (i.e., the target number is greater than the number of electrophysiology data points in the subset determined in block 606 because the user considers the initial subset under-inclusive). In response, system 8 can automatically modify the inclusion criteria to be more permissive/inclusive.

Conversely, moving slider 504 to the left of neutral can indicate that the user wants fewer of the collected electrophysiology data points to be included in the electrophysiology map (i.e., the target number is less than the number of electrophysiology data points in the subset determined in block 606 because the user considers the initial subset over-inclusive). In response, system 8 can automatically modify the inclusion criteria to be less permissive/inclusive.

According to aspects of the present disclosure, system 8 can compute the target number based on how far from the neutral position slider 504 is moved. For example, if slider 504 is moved to the right (i.e., the user indicates that more electrophysiology data points should be included in the electrophysiology map), the target number (denoted t) can be computed as $$t = \frac{k*(a-b)}{0.5*(n-1)},$$

where b is the number of electrophysiology data points in the subset determined in block 606, a is the total number of electrophysiology data points collected in block 604, n is the total number of notches 506 on sensitivity control 502 (e.g., eleven, as shown in FIG. 5), and k is the number of notches by which slider 504 has been moved. Thus, each notch 506 to the right of the neutral position on sensitivity control 502 adds the same number of previously-excluded electrophysiology data points to the electrophysiology map.

Conversely, if slider 504 is moved to the left (i.e., the user indicates that fewer electrophysiology data points should be included in the electrophysiology map), then the target number t can be computed as $$t = \frac{k*b}{0.5*(n-1)},$$

where the variables k, b, and n are defined as described above. Thus, each notch 506 to the left of the neutral position on sensitivity control 502 subtracts the same number of previously-included electrophysiology data points from the electrophysiology map.

In block 610, system 8 automatically modifies the inclusion criteria in response to the user's adjustment of slider 504 and the resultant computation of the target number of electrophysiology data points from block 608.

In some embodiments of the disclosure, system 8 uses statistical distributions of the inclusion data for the electrophysiology data points in the subset determined in block 606 when modifying the inclusion criteria in block 610. More particularly, system 8 can use the statistical distributions to determine which (one or more) of the inclusion criteria defined in block 602 would require the smallest adjustment(s) in order to reach the target number of electrophysiology data points from block 608.

Next, in block 612, system 8 determines the subset of the plurality of electrophysiology data points (collected in block 604) that are associated with inclusion data that satisfies the modified inclusion criteria (as modified in block 610).

In decision block 614, the number of electrophysiology data points in the subset of the plurality of electrophysiology data points associated with inclusion data that satisfies the inclusion criteria as modified in block 610 is compared to the target number. If the target number has been met, no further adjustments to the inclusion criteria are necessary, and the resultant electrophysiology map can be displayed (block 616).

If, on the other hand, the number of electrophysiology data points in the subset has not reached the target number, and slider 504 was adjusted to be more strict (e.g., it was moved to the left of the neutral position on sensitivity control 502), then the process proceeds to decision block 618, where a check is made to determine if there are additional inclusion criteria that are not currently enabled (e.g., their check boxes are not selected in interface 322). If no additional inclusion criteria remain to be enabled, then system 8 can report an error and/or the total possible number of electrophysiology data points that can be included in the electrophysiology map in block 622 without adjusting the originally-defined inclusion criteria (i.e., as defined in block 602) beyond a preset threshold amount, which may differ from criterion to criterion, and which may be user defined or absolute (e.g., the limits of a slider for an individual inclusion criteria within interface 322).

As shown by the dashed line from decision block 614, the same outcome can occur if the number of electrophysiology data points in the subset has not reached the target number, and slider 504 was adjusted to be more permissive (e.g., it was moved to the right of the neutral position on sensitivity control 502).

If, on the other hand, there are additional inclusion criteria that can be enabled, then they can be enabled in block 624. When additional inclusion criteria are so enabled, they can be set initially to software nominal values, which would typically fall in the middle of the likely range of values for a particular inclusion criterion, or to user preset values.

In addition, the originally selected inclusion criteria can be reset to their original values (i.e., as defined in block 602) in block 624. The process can then return to block 612 as described above.

Figure 6B:
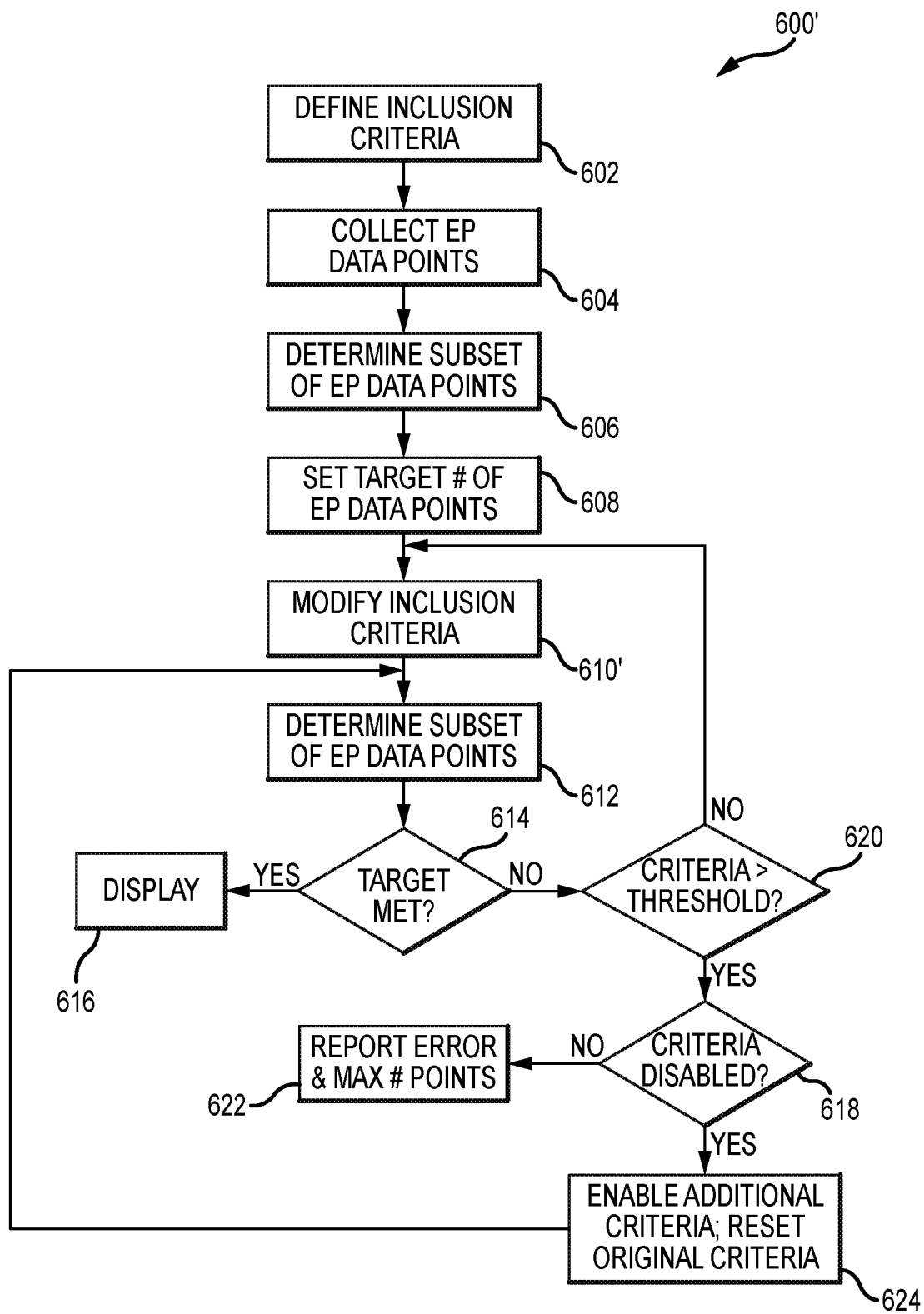
FIG. 6B is a flowchart depicting representative steps that can be followed in an alternative method of generating an electrophysiology map according to additional aspects of the teachings herein.

Another exemplary method of automatically adjusting inclusion criteria will be explained herein with reference to the flowchart 600' of representative steps presented as FIG. 6B. As shown in FIG. 6B, several steps are similar to those shown in FIG. 6A and discussed above.

In block 610', however, system 8 automatically makes incremental adjustments to one or more of the inclusion criteria defined in block 602 in order to reach the target number, with the direction of the incremental adjustments determined by the relationship between the target number and the number of electrophysiology data points in the subset determined in block 606 as described above. Each incremental adjustment can be about 1% to about 10% of the range of the respective inclusion criteria being adjusted.

Further, if the target number of electrophysiology data points is not met in decision block 614, the process proceeds to decision block 620, where a check is made to see if the modified inclusion criteria (i.e., as defined in block 610') differ from the original inclusion criteria (i.e., as defined in block 602) by more than a preset threshold amount, which may differ from criterion to criterion. If not, then the process can return to block 610' for another iteration of incremental adjustments to the inclusion criteria.

If the current modified inclusion criteria (i.e., as defined in block 610') do differ from the original inclusion criteria (i.e., as defined in block 602) by more than the preset threshold amount, then the process proceeds to decision block 618, discussed above. If no additional inclusion criteria remain to be enabled, then system 8 can report an error and/or the total possible number of electrophysiology data points that can be included in the electrophysiology map in block 622 without adjusting the originally-defined inclusion criteria (i.e., as defined in block 602) beyond the preset threshold amount.

If, on the other hand, there are additional inclusion criteria that can be enabled, then they can be enabled in block 624, provided, that slider 504 was adjusted to be more strict (e.g., it was moved to the left of the neutral position on sensitivity control 502). In addition, the originally selected inclusion criteria can be reset to their original values (i.e., as defined in block 602). The process can then return to block 612 as described above.

Although several embodiments of this invention have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, the computation of the target number of electrophysiology data points need not be linear (e.g., each notch 506 need not represent an addition or subtraction of the same number of previously excluded or previously included electrophysiology data points).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating an electrophysiology map of a portion of a patient's anatomy using an electroanatomical mapping system, comprising:
defining a plurality of inclusion criteria;
collecting a plurality of electrophysiology data points, each electrophysiology data point being associated with inclusion data;
the electroanatomical mapping system determining a subset of the plurality of electrophysiology data points having associated inclusion data that satisfies the plurality of inclusion criteria and that includes a number of electrophysiology data points;
setting a target number of electrophysiology data points from the plurality of electrophysiology data points for inclusion in the electrophysiology map of the portion of the patient's anatomy, the target number being different from the number of electrophysiology data points in the subset;
the electroanatomical mapping system automatically modifying the plurality of inclusion criteria; and
the electroanatomical mapping system determining a modified subset of the plurality of electrophysiology data points having associated inclusion data that satisfies the modified plurality of inclusion criteria and that includes a number of electrophysiology data points for inclusion in the electrophysiology map of the portion of the patient's anatomy,
wherein the electroanatomical mapping system automatically modifying the plurality of inclusion criteria comprises:
the electroanatomical mapping system automatically modifying the plurality of inclusion criteria to be more inclusive if the target number is greater than the number of electrophysiology data points in the subset of the plurality of electrophysiology data points having associated inclusion data that satisfies the plurality of inclusion criteria; and
the electroanatomical mapping system automatically modifying the plurality of inclusion criteria to be less inclusive if the target number is less than the number of electrophysiology data points in the subset of the plurality of electrophysiology data points having associated inclusion data that satisfies the plurality of inclusion criteria.

2. The method according to claim 1, further comprising:
iteratively repeating the steps:
the electroanatomical mapping system automatically modifying the plurality of inclusion criteria; and
the electroanatomical mapping system determining a modified subset of the plurality of electrophysiology data points having associated inclusion data that satisfies the modified plurality of inclusion criteria and that includes a number of electrophysiology data points for inclusion in the electrophysiology map of the portion of the patient's anatomy
until a first event to occur of:
the number of electrophysiology data points in the modified subset of the plurality of electrophysiology data points having associated inclusion data that satisfies the modified plurality of inclusion criteria reaches the target number of data points for inclusion in the electrophysiology map, and
the electroanatomical mapping system has automatically modified the plurality of inclusion criteria by a preset threshold amount relative to a state of the plurality of inclusion criteria prior to any modification by the electroanatomical mapping system.

3. The method according to claim 2, further comprising, if the first event to occur is the electroanatomical mapping system has automatically modified the plurality of inclusion criteria by a preset threshold amount relative to a state of the plurality of inclusion criteria prior to any modification by the electroanatomical mapping system:
the electroanatomical mapping system automatically resetting the plurality of inclusion criteria to the state of the plurality of inclusion criteria prior to any modification by the electroanatomical mapping system; and
the electroanatomical mapping system automatically adding one or more additional inclusion criteria to the plurality of inclusion criteria.

4. The method according to claim 3, further comprising, after the one or more additional inclusion criteria are added to the plurality of inclusion criteria:
iteratively repeating the steps:
the electroanatomical mapping system automatically modifying the plurality of inclusion criteria; and
the electroanatomical mapping system determining a modified subset of the plurality of electrophysiology data points having associated inclusion data that satisfies the modified plurality of inclusion criteria and that includes a number of electrophysiology data points for inclusion in the electrophysiology map of the portion of the patient's anatomy
until a first event to occur of:
the number of electrophysiology data points in the modified subset of the plurality of electrophysiology data points having associated inclusion data that satisfies the modified plurality of inclusion criteria reaches the target number of data points for inclusion in the electrophysiology map, and
the electroanatomical mapping system has automatically modified the plurality of inclusion criteria by a preset threshold amount relative to a state of the plurality of inclusion criteria prior to any modification by the electroanatomical mapping system.

5. The method according to claim 4, further comprising outputting an error if the first event to occur is the electroanatomical mapping system has automatically modified the plurality of inclusion criteria by a preset threshold amount relative to a state of the plurality of inclusion criteria prior to any modification by the electroanatomical mapping system.

6. The method according to claim 1, wherein setting a target number of electrophysiology data points from the plurality of electrophysiology data points for inclusion in the electrophysiology map of the portion of the patient's anatomy comprises:
displaying a graphical inclusion criterion sensitivity control at a neutral sensitivity;
accepting user input to adjust the graphical inclusion criterion sensitivity from the neutral sensitivity to an adjusted sensitivity; and
the electroanatomical mapping system automatically computing the target number of electrophysiology data points using the adjusted sensitivity and the number of electrophysiology data points in the subset of the plurality of electrophysiology data points having associated inclusion data that satisfies the plurality of inclusion criteria.

7. The method according to claim 6, wherein the electroanatomical mapping system further uses a number of electrophysiology data points in the plurality of data points in computing the target number of electrophysiology data points.

8. The method according to claim 1, further comprising: iteratively repeating the steps:
the electroanatomical mapping system automatically modifying the plurality of inclusion criteria; and
the electroanatomical mapping system determining a modified subset of the plurality of electrophysiology data points having associated inclusion data that satisfies the modified plurality of inclusion criteria and that includes a number of electrophysiology data points for inclusion in the electrophysiology map of the portion of the patient's anatomy
until the number of electrophysiology data points in the modified subset of the plurality of electrophysiology data points having associated inclusion data that satisfies the modified plurality of inclusion criteria reaches the target number of data points for inclusion in the electrophysiology map.

9. The method according to claim 8, further comprising generating a graphical representation of the electrophysiology map using the modified subset of the plurality of electrophysiology data points having associated inclusion data that satisfies the modified plurality of inclusion criteria.

10. The method according to claim 1, further comprising generating a graphical representation of the electrophysiology map using the modified subset of the plurality of electrophysiology data points having associated inclusion data that satisfies the modified plurality of inclusion criteria.

11. The method according to claim 1, wherein the electroanatomical mapping system automatically modifying the plurality of inclusion criteria further comprises the electroanatomical mapping system automatically adding an additional inclusion criterion to the plurality of inclusion criteria.

12. The method according to claim 1, wherein the electroanatomical mapping system automatically modifying the plurality of inclusion criteria further comprises the electroanatomical mapping system automatically adjusting all inclusion criteria of the plurality of inclusion criteria.

13. The method according to claim 1, wherein the electroanatomical mapping system automatically modifying the plurality of inclusion criteria comprises:
identifying a distribution of the inclusion data for the subset of the plurality of electrophysiology data points having associated inclusion data that satisfies the plurality of inclusion criteria; and
determining, using the distribution of the inclusion data, which inclusion criteria of the plurality of inclusion criteria would need to be adjusted a least amount when automatically adjusting the at least one inclusion criteria in order for the modified subset of the plurality of electrophysiology data points having associated inclusion data that satisfies the modified plurality of inclusion criteria to include the target number of electrophysiology data points.

14. A system for generating an electrophysiology map of a portion of a patient's anatomy, comprising:
an inclusion processor configured to:
receive as input a plurality of electrophysiology data points, each electrophysiology data point being associated with inclusion data;
receive as input a plurality of inclusion criteria;
receive as input a target number of electrophysiology data points for inclusion in an electrophysiology map;
determine a subset of the plurality of electrophysiology data points having associated inclusion data that satisfy the plurality of inclusion criteria;
automatically modify the plurality of inclusion criteria; and
determine a modified subset of the plurality of electrophysiology data points having associated inclusion data that satisfy the modified plurality of inclusion criteria,
wherein the inclusion processor is configured to automatically modify the plurality of inclusion criteria by:
automatically modifying the plurality of inclusion criteria to be more inclusive if the target number is greater than a number of electrophysiology data points in the subset of the plurality of electrophysiology data points having associated inclusion data that satisfy the plurality of inclusion criteria; and
automatically modifying the plurality of inclusion criteria to be less inclusive if the target number is less than the number of electrophysiology data points in the subset of the plurality of electrophysiology data points having associated inclusion data that satisfy the plurality of inclusion criteria.

15. The system according to claim 14, further comprising a mapping processor configured to generate a graphical representation of the electrophysiology map from the modified subset of the plurality of electrophysiology data points having associated inclusion data that satisfy the modified plurality of inclusion criteria.

16. The system according to claim 14, wherein the inclusion processor is further configured to iteratively automatically modify the plurality of inclusion criteria until a number of electrophysiology data points in the modified subset of the plurality of electrophysiology data points having associated inclusion data that satisfy the modified plurality of inclusion criteria equals the target number.

* * * * *